(12) United States Patent
Huber et al.

(10) Patent No.: US 11,020,831 B2
(45) Date of Patent: Jun. 1, 2021

(54) DENTAL MILLING MACHINE AND METHOD

(71) Applicant: DMU GmbH, Salzburg (AT)

(72) Inventors: Martin Huber, Pfarrwerfen (AT); Alfons Wörmer, Bischofshofen (AT)

(73) Assignee: DMU GMBH, Salzburg (AT)

( * ) Notice: Subject to any disclaimer, the term of this patent is extended or adjusted under 35 U.S.C. 154(b) by 0 days.

(21) Appl. No.: 16/229,071

(22) Filed: Dec. 21, 2018

(65) Prior Publication Data

US 2019/0192256 A1 Jun. 27, 2019

(30) Foreign Application Priority Data

Dec. 22, 2017 (EP) ..................................... 17210070

(51) Int. Cl.
| | | |
|---|---|---|
| *B23Q 1/70* | (2006.01) | |
| *B23Q 17/22* | (2006.01) | |
| *A61B 90/00* | (2016.01) | |
| *A61C 1/08* | (2006.01) | |
| *A61C 3/02* | (2006.01) | |

(Continued)

(52) U.S. Cl.
CPC ........... *B23Q 1/70* (2013.01); *B23Q 17/2241* (2013.01); *A61B 90/03* (2016.02); *A61B 2090/034* (2016.02); *A61C 1/082* (2013.01); *A61C 3/02* (2013.01); *A61C 13/0004* (2013.01); *A61C 13/0006* (2013.01); *B23Q 17/0923* (2013.01);

(Continued)

(58) Field of Classification Search
CPC ... B23B 31/20; B23B 31/201; A61C 13/0004; A61C 13/0006; A61C 13/0022; A61C 1/082; A61C 3/02; B23C 2226/18; B23Q 3/062
See application file for complete search history.

(56) References Cited

U.S. PATENT DOCUMENTS

| | | | | |
|---|---|---|---|---|
| 4,356,669 A | * | 11/1982 | Hoglund | ............... B24B 19/095 408/54 |
| 4,643,622 A | * | 2/1987 | Winski | ................. G05B 19/416 318/569 |

(Continued)

FOREIGN PATENT DOCUMENTS

| | | | | |
|---|---|---|---|---|
| CA | 2935770 A1 | * | 7/2015 | ......... A61C 13/0022 |
| DE | 102013100155 A1 | | 7/2014 | |

(Continued)

*Primary Examiner* — Nicole N Ramos
(74) *Attorney, Agent, or Firm* — Ann M. Knab; Thad McMurray

(57) ABSTRACT

A dental milling machine is provided with a tool which is guided in a chuck. A workpiece arm is mounted opposite the tool to be able to be moved at least in the direction of the spindle axis. With a control device it can be moved in relation to the workpiece, especially by means of a drive motor at the workpiece arm. The workpiece arm has an abutment element, whereby the control device moves the tool and the abutment element towards each other until they abut each other. The control device can be used to detect abutment of the abutment element with respect to the tool, in particular with respect to its tip, in particular by decelerating the (relative) movement of the tool and the abutment element towards each another, upon contact of the tool and the abutment element. This position may be signaled as a reference position and, especially may be stored.

13 Claims, 4 Drawing Sheets

(51) Int. Cl.
  *A61C 13/00* (2006.01)
  *B23Q 17/09* (2006.01)
(52) U.S. Cl.
  CPC .............. *G05B 2219/45167* (2013.01); *G05B 2219/45172* (2013.01)

(56) References Cited

U.S. PATENT DOCUMENTS

| | | | | |
|---|---|---|---|---|
| 4,944,643 | A * | 7/1990 | Lehmkuhl | B23B 31/006 279/145 |
| 5,372,568 | A * | 12/1994 | Matsuoka | B23B 31/263 483/56 |
| 5,781,983 | A * | 7/1998 | Gruner | B23Q 7/047 29/563 |
| 8,820,726 | B2 * | 9/2014 | Yeom | B23Q 3/061 269/55 |
| 9,801,701 | B2 | 10/2017 | Schnitzspan et al. | |
| 9,939,806 | B2 | 4/2018 | Leeson et al. | |
| 10,088,832 | B2 | 10/2018 | Tanigawa et al. | |
| 10,133,244 | B2 | 11/2018 | Leeson et al. | |
| 2011/0280692 | A1 * | 11/2011 | Evertz | B23Q 11/0891 414/222.07 |
| 2013/0216323 | A1 * | 8/2013 | Reck | A47B 97/04 483/56 |
| 2016/0072418 | A1 * | 3/2016 | Oberthur | G01D 5/2093 318/685 |
| 2016/0074946 | A1 * | 3/2016 | Hertel | B23C 1/14 409/132 |
| 2018/0236620 | A1 | 8/2018 | Schüle et al. | |

FOREIGN PATENT DOCUMENTS

| | | | | |
|---|---|---|---|---|
| DE | 202015100312 | U1 | | 3/2015 |
| EP | 0474588 | A1 | | 3/1992 |
| GB | 1435890 | A | * | 5/1976 ......... G05B 19/4181 |
| WO | WO-2010081712 | A1 | * | 7/2010 ........... B23Q 1/5406 |

\* cited by examiner

DENTAL MILLING MACHINE AND METHOD

CROSS-REFERENCE TO RELATED APPLICATIONS

This application claims priority to European patent application No. 17210070.3 filed on Dec. 22, 2017, the disclosure of which is incorporated herein by reference in its entirety.

FIELD OF THE INVENTION

The invention relates to a dental milling machine as well as a process for operating such a machine.

BACKGROUND

Milling machines typically include several axes of motion for a workpiece, and, if necessary, also include one or more axes of motion for the tool. Dental milling machines that have a 5/0 distribution of the axes, i.e. five motion axes for the workpiece and none for the tool, have proven to be particularly favorable. Examples of milling machines and processes are set forth in U.S. Pat. Nos. 10,088,832, 10,133,244, 9,939,806, 9,801,701, and US patent application No. 20180236620, all of which are herein incorporated by reference in their entirety.

Knowing the working point, i.e. the point of contact between the workpiece and the tool, is essential for accuracy of machining. For this purpose, the milling machine will typically be calibrated.

Even tools that are manufactured with comparatively small tolerances are subject to wear. In addition, the clamping position in the chuck is not always the same, so that calibration of the clamped tool must be carried out on a regular and recurrent basis by recording a reference position.

Tool length measurement systems are the core components of fully automated CNC machines. However, conventional tool length measuring systems are not suitable for very small CNC machines as they do not represent a cost-effective solution.

DE 10 2013 100 155 A1 discloses a mechanical interface for coupling one module to a module support or for coupling two modules comprising a first interface component, a second interface component, the interface components being complementary, a positioning means for repeatedly positioning the second interface component and the first interface component, and a positioning means for repeatedly positioning the second interface component and the first interface component in relation to each other, and holding means for holding the second interface component to the first interface component, the interface comprising data transfer means for transferring data between the first interface component and the second interface component, and power transfer means for transferring electrical power between the first interface component and the second interface component.

SUMMARY

Thus, the object of the invention is to provide an improved dental milling machine and an improved method of operating a dental milling machine, which enables the dental milling machine to be automatically calibrated and, by measuring a tool length of a milling tool, to incorporate manufacturing tolerances of the milling tool into the calibration of the dental milling machine.

This task will be solved by a dental milling machine having the features of the attached claims. Furthermore, the problem will be solved by a method having the features of the attached claims.

The present invention provides for a dental milling machine comprising a tool which is guided in a chuck, the chuck especially being rotatably mounted, but is otherwise fixedly mounted to the machine. An abutment or contact element is provided on a workpiece arm which is mounted so as to be movable in relation to the tool at least in the direction of the spindle axis, and a control device is provided which detects abutment or contact between the abutment element and the milling tool, especially at the tip thereof, by moving the tool and the abutment element towards each other to abut each other and the control device detects the contact of the abutment element at the tool by decelerating the (relative) movement upon contact thereof. This position is stored as the reference position. The abutment element is mounted on a workpiece arm especially spaced apart from the workpiece axis.

Said movement can be carried out such that either the tool is clamped to a stationary drive spindle while the workpiece arm including the abutment element are being moved, or such that the workpiece arm remains stationary while the tool is being moved towards it. The drive motor for the tool is preferably switched off. However, it is also possible for the tool to rotate slowly.

The tool can be moved by a drive motor that is constructed as a stepping motor and is connected to an encoder, wherein a loss of step of the stepping motor detected by the encoder is signaled or detected as abutment of the abutment element on the tool.

The invention also provides for a process for operating a dental milling machine. The process involves providing a tool which is guided in a chuck, the chuck thus being especially rotatable, but is otherwise fixedly mounted to the machine, and the milling tool being clamped in the chuck. An abutment element mounted on the tool arm is mounted such that it is able to move in relation to the tool at least in the direction of the spindle axis.

The process also includes the provision of a control device, which detects a contact between the tool and the contact element. For this purpose, the motor current for the drive of the workpiece arm is reduced when approaching the tool. The workpiece arm thus moves with less force while avoiding damage to the tool.

The movement is decelerated when contacting the workpiece. This is detected by an encoder that is mechanically coupled to the axis of the drive motor. The output signal thereof is transmitted to the control device. In this respect, the control device and the system element form a sensor.

In one aspect, the present invention provides a precise measurement of the length of the milling tool of the dental milling machine by providing the sensor. It is especially advantageous for the sensor to be incorporated into the dental milling machine, and the length data concerning the length of the milling tool can be obtained via the sensor itself in connection with a corresponding evaluation device. The need for an external measuring device, such as an optical measuring device may thus be omitted.

This allows for providing a precise reference position to process the workpiece in the dental milling machine, and precise reference positioning automatically during each tool replacement, by performing the method according to the invention. The position determined by the contact precisely corresponds to the point where the tool will subsequently process the workpiece.

Contact with the abutment element may occur precisely in the spindle axis, i.e. centrally, or slightly offset, i.e. laterally offset by less than the tool diameter. It is also possible to define two reference points, i.e. one point centrally offset and one point laterally offset. This not only allows the length but also the shape of the tool at its tip to be determined and recognized.

This is especially important for a worn-in-part insert.

The solution of the invention enables measuring a new insert, both its absolute length starting from the shaft and also the clamping length thereof, i.e. the current reference position in the clamped state, and the same applies to a tool that has already been used and re-clamped.

The solution of the invention is preferably applied to every tool replacement.

Advantageous embodiments and further developments thereof will arise from the subclaims as well as from the description while making reference to the figures.

According to a preferred embodiment, a milling tool detection device is provided, which records the respective milling tool by means of a code, especially an optical two-dimensional code, especially preferably a Data-Matrix-Code, wherein the milling tool is measured in advance and its length is stored, especially, also, in the control device. Thus, the milling tool can safely and reliably be measured.

According to another preferred embodiment, a temperature-measuring device is provided and the control device having a memory for an expansion coefficient table, which stores the experimentally determined expansion coefficient of the milling tool based on a temperature change and indicates the precise position of the tip of the milling tool based on this change in length. Thus, the position of the tip of the milling tool is advantageously known and therefore only the position of the tip of the tool is required to be detected by the encoder that detects the movement of the abutment element to measure the precise length of the milling tool.

According to another preferred embodiment, nozzles are provided, which are configured to direct a jet of liquid towards the milling tool for wet-processing of a workpiece, and the nozzles are configured to release compressed air into an environment. Thus, the nozzles can advantageously be used for a plurality of purposes.

The described configurations and further embodiments can be combined with each other as desired.

Further possible configurations, embodiments and implementations of the invention also include combinations of features of the invention not explicitly described above or in the following while making reference to the embodiment examples.

BRIEF DESCRIPTION OF THE DRAWINGS

The associated drawings are intended for a better understanding of the embodiments of the invention. They are to illustrate the embodiments and to explain the principles and concepts of the invention in connection with the description.

Other embodiments and many of the advantages mentioned will arise from the drawings. The elements illustrated in the drawings are not necessarily to scale, wherein.

DETAILED DESCRIPTION

In the figures of the drawings, equal reference numbers denote equal or functionally equivalent elements, components or units, unless otherwise indicated.

Figure 1:
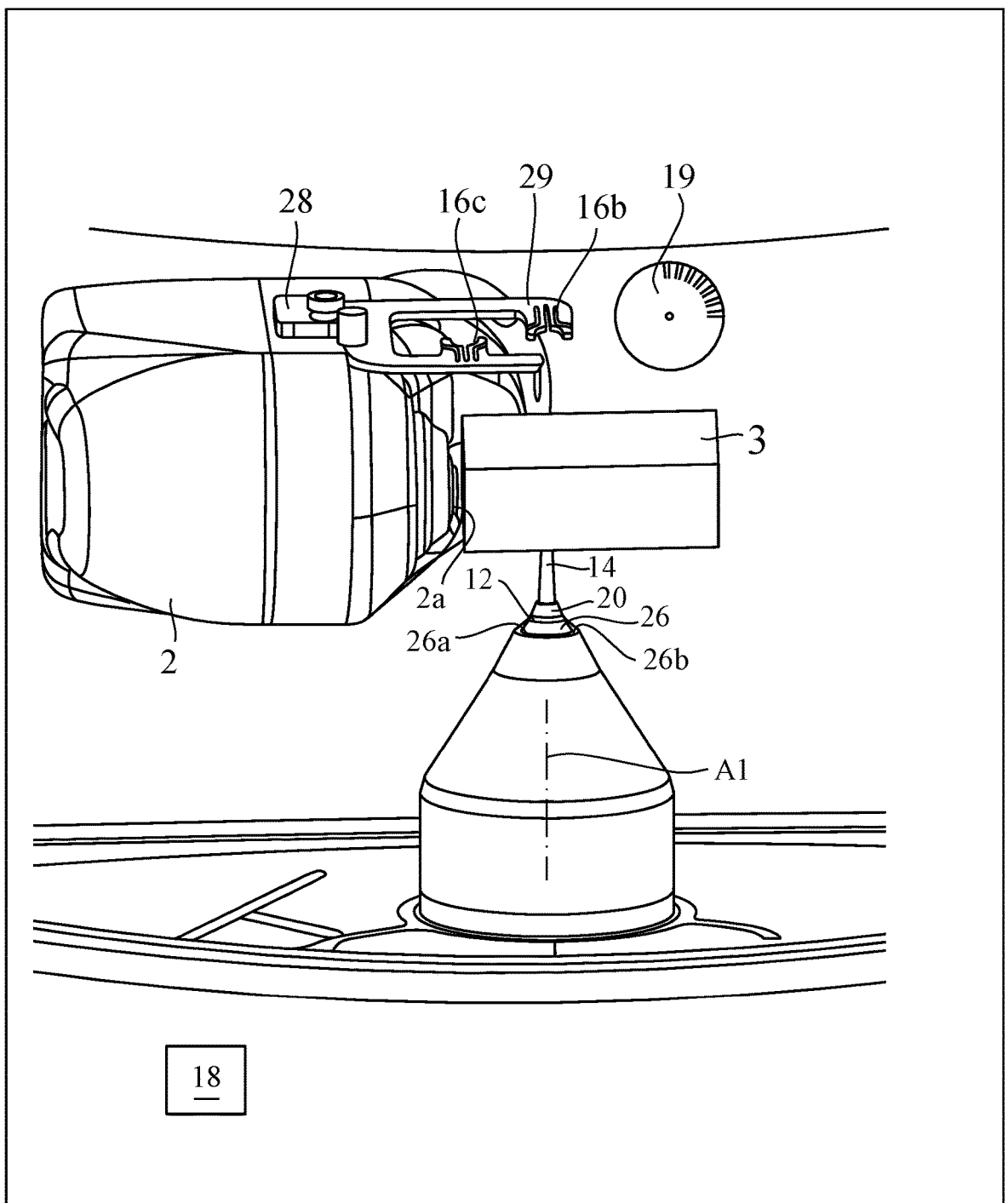
FIG. 1 is a perspective schematic representation of the dental milling machine in accordance with a preferred embodiment of the invention, in the processing state.

FIG. 1 shows a schematic representation of the dental milling machine according to a preferred embodiment of the invention.

Figure 5:
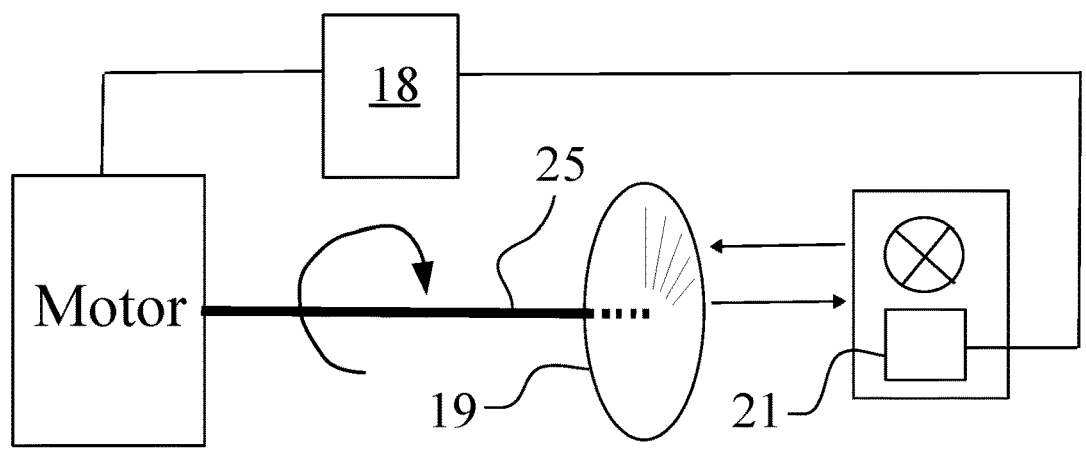
FIG. 5 is an illustration of the workpiece holder according to the invention.

The dental milling machine 1 comprises a tool 14, which is guided in a chuck 12. The dental milling machine 1 also comprises a robot arm, herein referred to as workpiece arm 2, which is provided with a chuck 2a, into which a workpiece 3 with a corresponding workpiece holder 4 can be inserted, as shown in FIG. 5. FIG. 5 shows the workpiece 3 attached to workpiece holder 4, which workpiece holder 4 is inserted into chuck 2a.

Specifically, the chuck 12 can be rotated, but is otherwise fixedly mounted to the machine. The milling tool 14 is clamped into the chuck 12 via its invisible shaft.

The workpiece arm 2 is mounted opposite to the tool 14 such that it can move at least in the direction of a spindle axis A1. In addition, the dental milling machine 1 has a control device 18. The control device 18 is configured to detect the relative position of the workpiece arm 2 in relation to the milling tool 14 via an encoder 19, which is coupled to a drive motor of the workpiece arm 2, which mechanics are discussed below in reference to FIG. 4.

The milling tool 14 has a ring 20 formed therein. The ring 20 is arranged at a distance from the tip 14a of the milling tool 14 and serves as a stop when clamping into the chuck 12.

The ring 20 is mounted to the milling tool 14 at the transition portion to its shaft 23. The shaft 23 has a flat surface with an accuracy of especially 15 μm, in relation to the distance D to the tip of the milling tool. The tip 14a of the milling tool preferably is equipped with a diamond. Alternatively, other tips 14a, such as metal tips, can be provided.

A milling tool detection device 22 is provided. The milling tool detection device 22, for example a camera, detects the respective milling tool 14 by means of a code, especially an optical two-dimensional code, such as a Data-Matrix-Code. The milling tool is measured in advance and the distance D thereof between the ring 20 and the tip 14a of the milling tool 14 is stored, especially also in the control device 18. Furthermore, the dental milling machine 1 comprises a sensor or temperature-measuring device 24. The control device 18 comprises a memory for an expansion table, which stores the experimentally determined expansion of the milling tool based on a temperature change, and indicates the precise position of the tip of the milling tool based on this change in length.

The ring 20 especially comprises a groove through which a tool replacement arm, for example the tool changer or gripper holder 29 on the workpiece arm 2, can engage into the milling tool 14, thus removing the milling tool from the chuck. In the state of being mounted therein, the tool can be guided in front of the camera 22 so as to perform the above-described milling tool detection.

The substantially annular surface 26 surrounding the chuck also comprises a plurality of nozzles 26a. On the one hand, the nozzles 26a have the function of directing a jet of liquid to the milling tool 14, enabling wet processing of a workpiece by the milling tool 14. In addition, the nozzles 26a have the additional function of delivering compressed air to an environment through the nozzles 26a. By expelling compressed air through the nozzles 26a, the ring 20 or the milling tool 14 can be cleaned from impurities.

Figure 2:
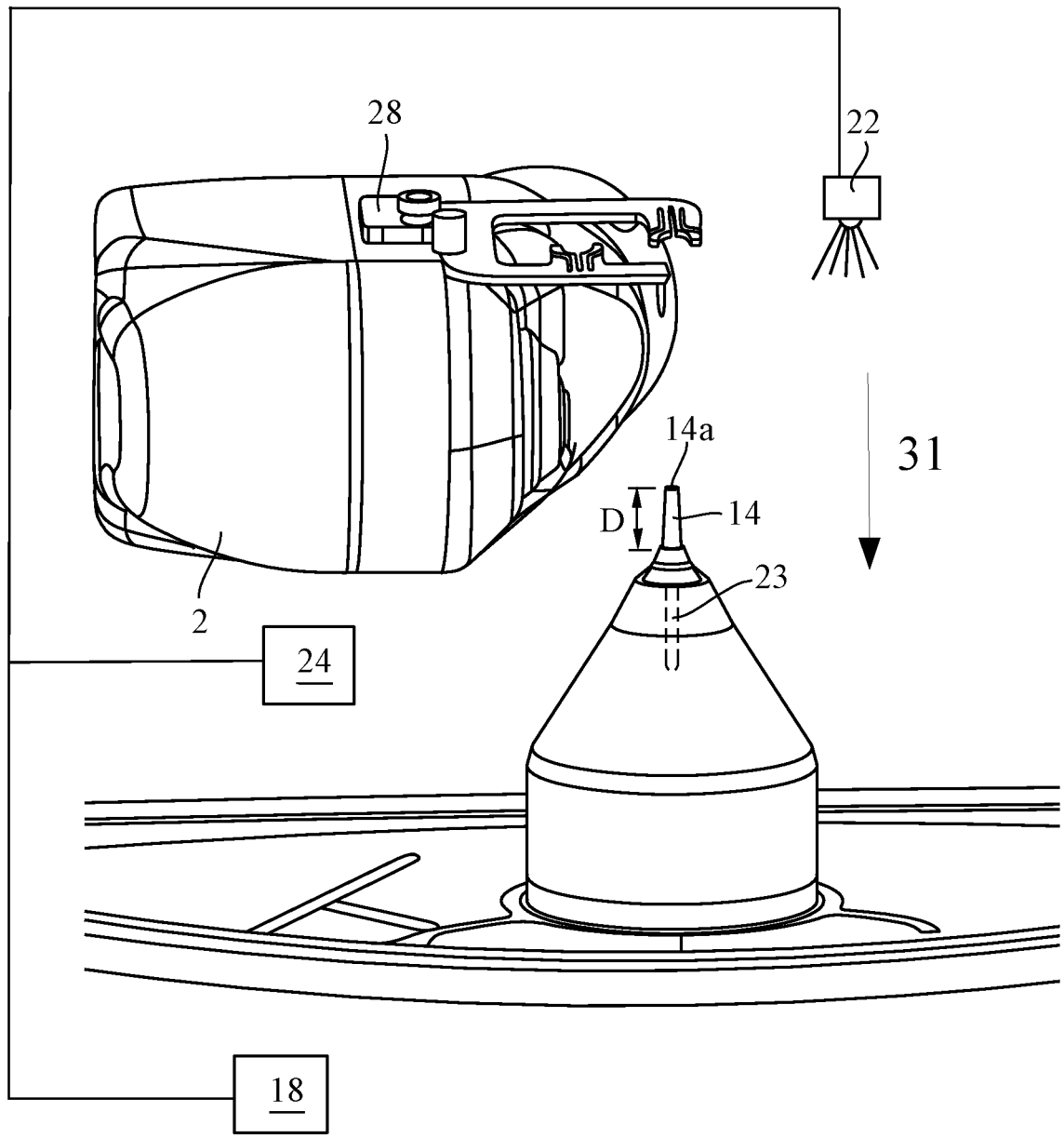
FIG. 2 is an illustration of the dental milling machine shown in FIG. 1, but devoid of the workpiece, illustrating the abutment element according to the invention.

FIGS. 1 and 2 show a schematic representation of a contact or abutment element 28 attached to the workpiece arm 2 to measure a length of the milling tool according to the preferred embodiment of the invention. The abutment element 28 is configured as an essentially flat metal sheet and will be described in more detail below. It is mounted adjacent to or together with the gripper holder 29 for a milling tool 14.

The gripper holder 29 for the milling tool 14 has a first holding element 16b and a second holding element 16c. The first holding element and the second holding element are configured such that the first holding element 16b or the second holding element 16c can engage into the respective milling tool 14 in the region of one of the grooves of the ring 20, the groove of the ring 20 of the milling tool 14 being able to engage into the first holding element 16b or the second holding element 16c.

The first holding element 16b and the second holding element 16c are arranged offset with respect to one another on the workpiece arm 2, such that a milling tool 14 is inserted, for example, in the holding element 16c, another milling tool, which is arranged in the chuck 12, can be removed from the chuck 12 by the first holding element 16b, and, in a subsequent working step, the milling tool 14 inserted in the holding element 16c can be transferred into the then unloaded chuck 12.

Figure 3:
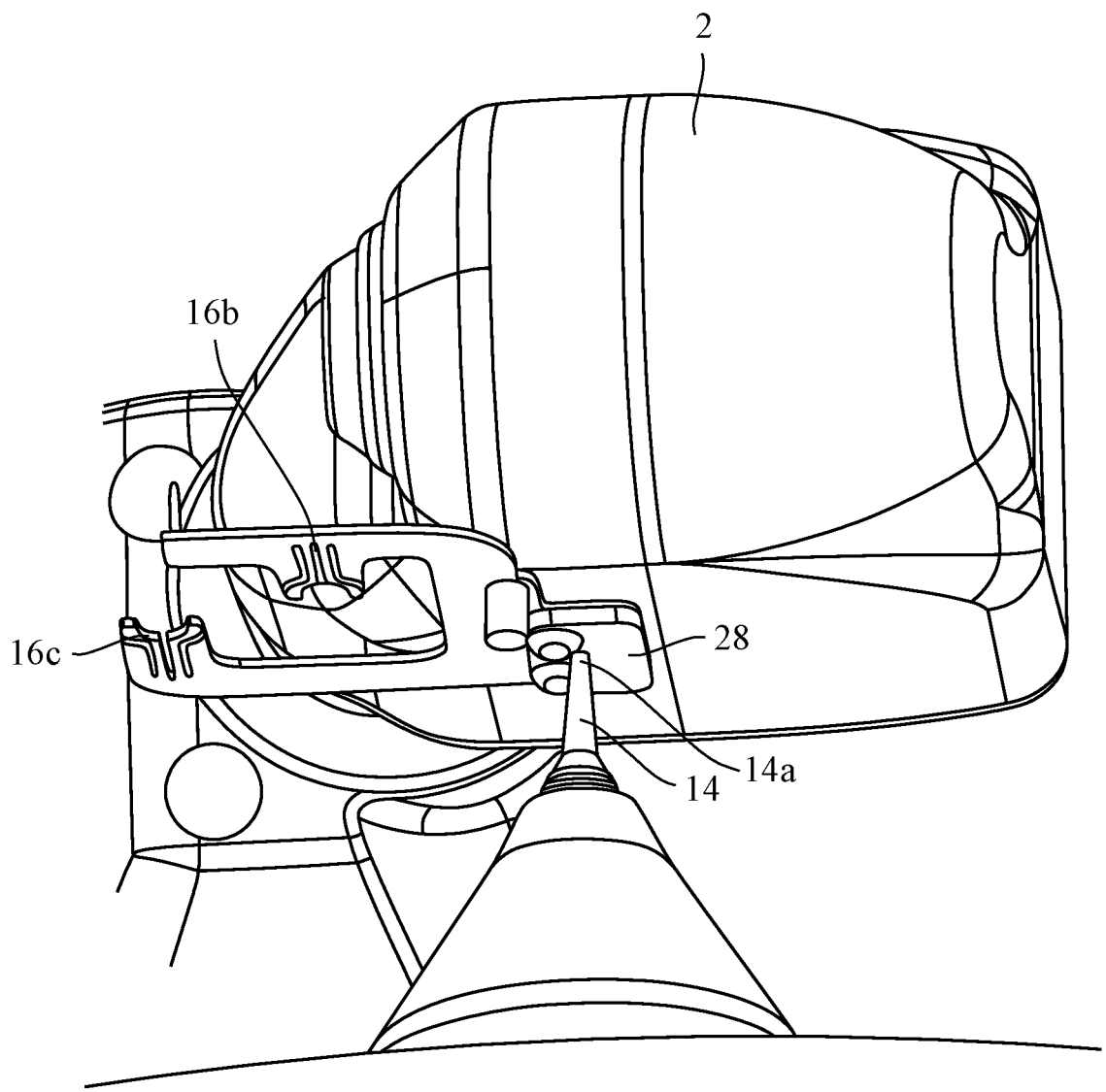
FIG. 3 is an illustration of the abutment element according to the invention for recording a length and/or position of the milling tool according to the preferred embodiment of the invention.

In the position shown in FIG. 1, the abutment element 28 is at the top of the workpiece arm 2. The workpiece arm 2 can spatially be moved along five axes, and, among others, can also be rotated so that the abutment element 28 can be located at the bottom (FIG. 3).

The abutment element is attached at the side of the workpiece at 2. FIG. 2 shows a state of the dental milling machine according to the invention, which allows a reference position to be determined.

In this state, it is not required for the workpiece arm 2 to carry a workpiece 3.

Reference point determination refers to the determination of the actual position of the tip 14a of tool 14 in relation to the workpiece arm in which the workpiece 3 will subsequently be clamped.

Even if the workpiece arm 2 herein is shown as being movable and the tool 14 is shown with its spindle motor being fixedly mounted in space, it is to be understood that kinematically inverse mounting is also possible without leaving the scope of the invention.

Basically, the reference position is determined so that the workpiece arm 2 is lowered with the abutment element 28 facing downwards in the direction of the arrow 31 until the abutment element 28 contacts the tool 14.

The contact position is also shown in FIG. 3. The abutment element 28 preferably consists of hardened sheet steel and is mounted with high precision on the workpiece arm 2. The tip 14a of tool 14 meets the abutment element 28 at a planar point.

It is to be understood that, if required, a second reference detection can also be performed by detecting the wear of the tool 14 at its tip by inclining the abutment element 28.

The system preferably is detected via a slip sensor. Encoder 19, which is coupled to the drive motor for the vertical movement of the workpiece arm 2, is used for this purpose.

The encoder 19 emits signals for moving the workpiece arm 2 in the direction of the tool tip 14a.

For reference position detection, the drive motor now is supplied with a lower drive current than usual. This enables smooth downward movement. Encoder 19 detects the linear movement and sends the corresponding signals to control device 18.

When the abutment element 28 is in contact with the tool 14, the encoder 19 only emits those signals, which correspond to a downward movement of the workpiece arm 2. The drive motor tries to move the abutment element 28 downwards, but does not succeed in doing this as it is in contact with tool 14.

Accordingly, there is a slip between the control signal for the drive motor, also emitted by control device 18, and the control signal for the actual movement, corresponding to the signals from encoder 19.

The first time a drive step is skipped, i.e. the first slip, is now detected and evaluated by the control device to indicate abutment between the tool and the abutment piece and will be signaled accordingly.

Figure 4:
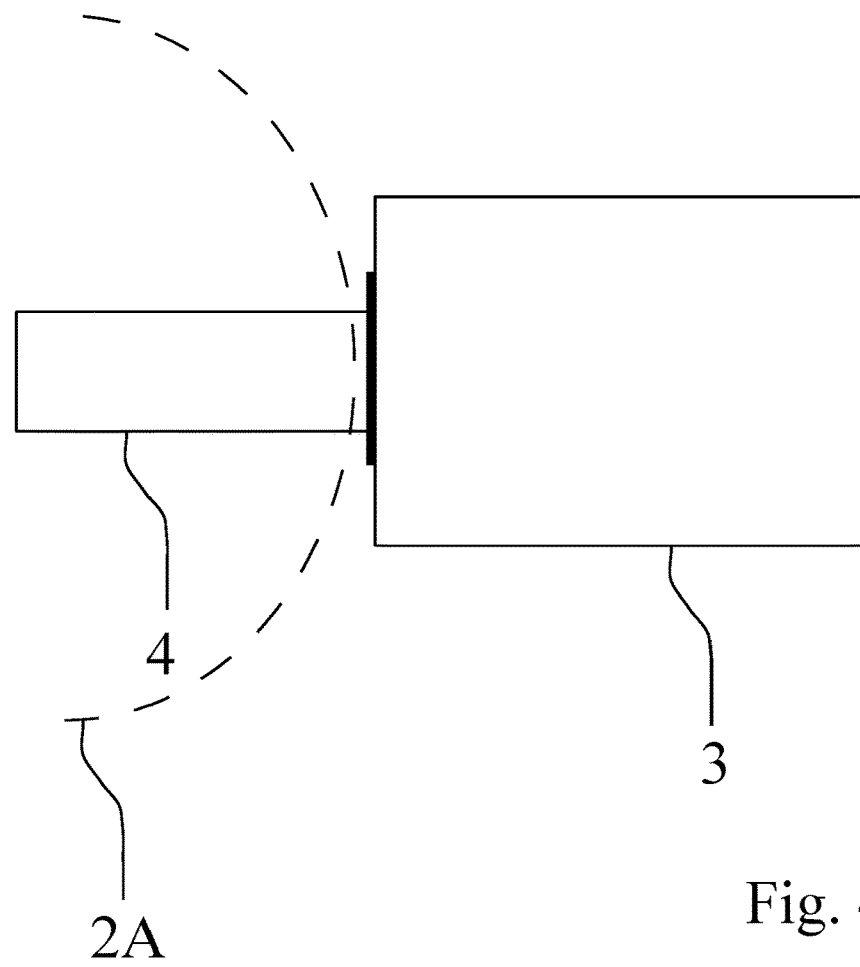
FIG. 4 is a block diagram showing the connection of various components in the dental milling machine in accordance with the invention.

The principle of the encoder 19 is further illustrated in FIG. 4. Encoder 19 is to detect transitions between (e.g., dark) lines being printed onto a (e.g., lightly colored, pale or white) disc of the encoder. When one motor of the workpiece arm 2 is turning due to respective control commands being sent from the control unit 18, the encoder disc is turning the same way since it is fixedly mounted on the motor axis 25. When turning, the lines printed on the encoder disc pass the light source and sensor 21. Sensor 21 is detecting the change of the reflected light due to the continuous change between the dark line and light background color of the enclosure disc. These transitions between light and dark are used to derive a degree of the motion of the encoder disc and thus of the motor axis 25.

In normal operation sensor 21 is to detect the actual motion of the motor axis 25 and to send its output signal to the control unit 18. Thus, exact positioning of the workpiece arm (2) is possible by analyzing the output signals of all encoders being attached, one to each motor axis (which is not limited to any number of axes, but including as many as necessary, such as 5 encoders and respective output signals for a 5/0 CAM device).

In the reference position detection operation according to the present invention, it is further detected whether a control command instructing a motor to turn causes a respective encoder/sensor output signal. In the case that the tip of the tool (14) is already in contact with the contact or abutment element (28), the motor is not able to move further which means that no further sensor signal change can be detected. This is referred to as slip. When such a slip is detected, the reference position can be stored by the control unit (18).

In an advantageous further embodiment, the drive motor is operated in normal operation in an open loop mode, which has advantages in speed. For reference determination, however, it is preferably operated in the closed-loop mode.

The recorded reference position is also stored and can be used to calibrate the dental milling machine to the tool 14 as measured.

The tool-specific code also allows the operating hours of the tool to be recorded by the control device 18. If the tool 14 is used again after only a few operating hours, it may not be required to re-measure it, i.e. to determine a new reference point. However, this can of course be done if required.

Although this invention has been described above while making reference to the preferred examples, it is not limited thereto, but can be modified in many ways. In particular, the invention may be varied or modified in various ways without deviating from the core of the invention.

For example, dimensioning or the geometric or material configuration of the position sensor can be varied or adapted to the respective structural requirements of the dental milling machine.

The invention claimed is:

1. A dental milling machine comprising
    a tool which is guided in a chuck, wherein the chuck is rotatably mounted and fixedly mounted to the dental milling machine,
    a workpiece arm mounted to move in relation to the tool at least in the direction of a spindle axis of the tool, and
    a control device configured to move the tool in relation to a workpiece,
    wherein the workpiece arm includes an abutment element, spaced apart from a workpiece axis, wherein the control device is configured to move the tool and the abutment element towards each other to abut each other,
    wherein the tool is moved by a drive motor that is constructed as a stepping motor and is connected to an encoder,
    wherein the control device is configured to detect contact or abutment of the abutment element against the tool by loss of step of the stepping motor detected by the encoder.

2. The dental milling machine according to claim 1,
    wherein the tool comprises a tip and
    wherein abutment of the abutment element against the tool is at the tip of the tool.

3. The dental milling machine according to claim 1,
    wherein the control device decelerates the movement of the tool and the abutment element towards each other upon contact of the tool and the abutment element, and
    wherein the contact is a position that is signaled and stored as a reference position.

4. The dental milling machine according to claim 1, wherein the tool comprises a tip.

5. The dental milling machine according to claim 4,
    wherein the abutment of the tool with the abutment element is at the tip of the tool.

6. The dental milling machine according to claim 2,
    wherein the drive motor for determining the reference position at the tip of the tool is operated at a reduced a drive current when approaching the abutment element.

7. The dental milling machine according to claim 1,
    wherein the abutment element is laterally mounted on the workpiece arm, spaced apart from the axis of the workpiece by a predetermined amount and also spaced apart from the workpiece.

8. The dental milling machine according to according to claim 2,
    wherein the control device directs relative movement of the abutment element and the tip of the tool as a linear, translational movement to and from the tool.

9. The dental milling machine according to claim 2,
    wherein the control device directs the workpiece arm including the abutment element towards the tip of the tool such that the abutment element always contacts the tip of the tool at the same location, even during tool replacement.

10. The dental milling machine according to claim 1,
    wherein the dental milling machine is configured as a 5/0 machine tool comprising five axes of movement for the workpiece arm.

11. The dental milling machine according to claim 4,
    wherein, for reference point determination of the contact between the abutment element and the tool, the control device switches the encoder of the drive motor of the tool arm from open loop to closed loop.

12. The dental milling machine according to claim 4,
    wherein combination of the control device and the encoder is configured as a slip sensor, through which the control device detects or signals the contact of the abutment element with the tool tip when slip occurs during movement of the workpiece arm towards the tool tip.

13. The dental milling machine according to claim 1,
    wherein the milling tool comprises a code, and
    wherein a milling tool detection device specifically detects the milling tool on the basis of the code, and the detection is stored in the control device.

* * * * *